United States Patent
Kormann et al.

(10) Patent No.: US 7,265,831 B2
(45) Date of Patent: Sep. 4, 2007

(54) SPECTROMETRIC MEASURING HEAD FOR HARVESTING MACHINES AND OTHER EQUIPMENT USED IN AGRICULTURE

(75) Inventors: Georg Kormann, Zweibrucken (DE); Werner Flohr, Kaiserslautern-Dansenberg (DE); Nico Correns, Weimar (DE); Michael Rode, Jena (DE); Werner Hoyme, Gebstedt (DE); Martin Götz, Jena (DE)

(73) Assignee: Deere & Company, Moline, IL (US)

( * ) Notice: Subject to any disclaimer, the term of this patent is extended or adjusted under 35 U.S.C. 154(b) by 120 days.

(21) Appl. No.: 11/215,503

(22) Filed: Aug. 30, 2005

(65) Prior Publication Data

US 2006/0093522 A1    May 4, 2006

(30) Foreign Application Priority Data

Sep. 30, 2004    (DE) ...................... 10 2004 048 103

(51) Int. Cl.
*G01J 3/28*    (2006.01)
(52) U.S. Cl. .................................. 356/328; 250/339.07
(58) Field of Classification Search ................ 356/326, 356/328; 250/339.06, 339.07
See application file for complete search history.

(56) References Cited

U.S. PATENT DOCUMENTS 6,418,805 B1    7/2002    Carney et al. ................ 73/866

2002/0039186 A1    4/2002    Rosenberg ................... 356/432

FOREIGN PATENT DOCUMENTS

| EP | 0 908 087 B1 | 7/2002 |
|---|---|---|
| EP | 0 960 557 B1 | 9/2003 |
| EP | 1 053 671 B1 | 6/2004 |
| WO | 99/40419 | 8/1999 |
| WO | 99/58959 | 11/1999 |
| WO | WO99/58959 | 11/1999 |
| WO | WO 00/04373 | 1/2000 |
| WO | WO 2005/106431 | 11/2005 |

OTHER PUBLICATIONS

DE 10 2004 021 448.4, Spektrometrischer Reflexionsmesskopf und Verfahren zu dessen Interner Rekallbrierung, unpublished file.

*Primary Examiner*—F. L. Evans

(57) ABSTRACT

A spectrometric measuring head for harvesting machines and other agricultural equipment comprises a housing with a window, in which a light source, a spectrometer arrangement and at least two standards for internal recalibration are provided. The standards can optionally be swiveled in the optical path of the measuring head such that the entire measuring light coming from the light source is used for recalibration. A processor that captures and processes the measured values and an interface to a bus system are arranged in the housing.

9 Claims, 1 Drawing Sheet

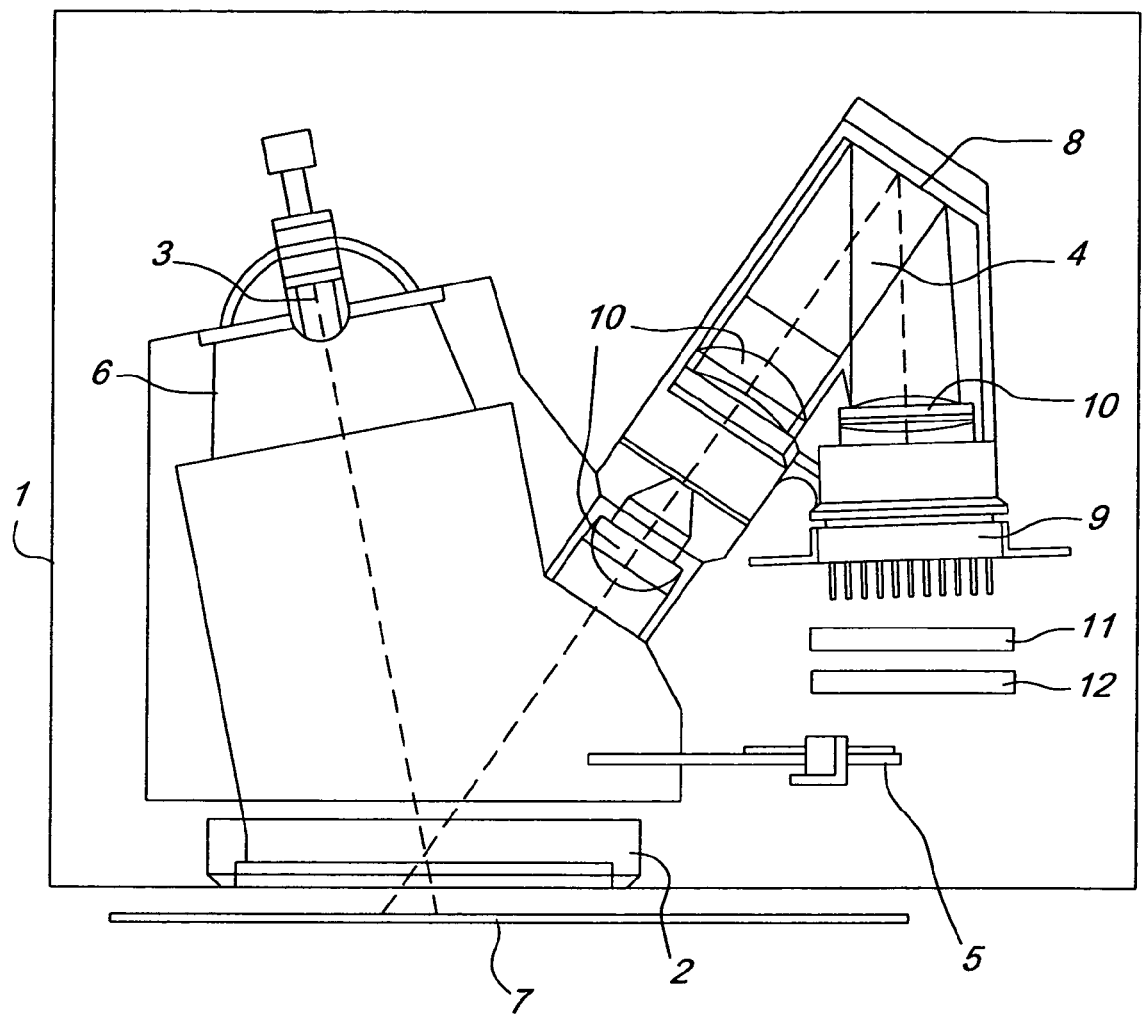

SPECTROMETRIC MEASURING HEAD FOR HARVESTING MACHINES AND OTHER EQUIPMENT USED IN AGRICULTURE

FIELD OF THE INVENTION

The present invention relates to a device for measuring the constituents of harvested agricultural products, wherein the measurements can be performed both statically and based on a material flow. The spectrometric measuring head is provided for use on harvesting machines and other equipment used in agriculture, wherein either the crop flows past the measuring head or the measuring head is moved past the crop. Using the measurement results different contents such as moisture, protein, starch or oil and properties such as cutting length, fiber state or temperature of the product can be determined based on calibrations.

BACKGROUND OF THE INVENTION

Among the numerous systems known in the state of the art for analyzing the constituents of harvested agricultural products, spectroscopy in the near infrared range (NIR) has prevailed due to various advantages. Compared to an analysis of the constituents using familiar laboratory methods, which may take several hours, NIR spectroscopy provides initial analysis results already within thirty to sixty seconds. Moreover the analyzed samples are not changed or destroyed by the spectrophotometric techniques.

In a typical spectroscopic analysis, samples are exposed to radiation of pre-selected wavelengths and their transmission and/or reflection power is measured. For example filter wheels, diode arrays or diffraction gratings are used to generate the required specific wavelengths.

Due to mobile parts, filter wheels and scanning diffraction gratings are sensitive to vibrations and not reliable when they analyze grain during harvesting. Consequently they are not suited for use on combines or other agricultural harvesting machines, which generate mechanical vibrations.

A device and a method for measuring moisture in harvesting machines is revealed in EP 0 908 087 B1. Here the moisture measuring device is combined with a sensor condition control device in order to forego the otherwise required measuring product-related and processing-related calibrations. Combining the moisture sensor with a sensor condition control device makes it possible to detect erroneous conditions when determining the moisture signal, point them out, initiate corrective action and/or perform a calibration. The sensor condition control device comprises microprocessors as well as suitable evaluation software and can trigger different corrective, display or calibrating measures as a function of the determined measurement status (with plausibility check). For example additional information regarding the crop (e.g. corn, wheat, barley etc.) with corresponding supplemental information (dry, wet, high amount of weeds) can be specified using an input or memory element. This information is taken into consideration in the evaluation of the determined measured values. For this purpose, the moisture sensors arranged in a housing convey the measured moisture values of the conveyed crop. The sensors consist, for example, of an electrode and an electronic system. The suggested solution however only relates to the determination and documentation of the measured moisture values of the crop. No statements can be made about the composition of the crop.

Also the method described in EP 0 960 557 B1 relates to the measurement of crop humidity on a harvester. Here especially the data of a moisture sensor are combined with the data of a mass flow rate sensor and compiled in a map illustrating the deduced moisture content in several areas of the field. The crop's moisture content here is determined by means of its electric conductivity. In this solution as well no statements can be made about the composition of the crop.

Unlike the solutions mentioned above, the documents WO 99/040419 and WO 99/058959 describe arrangements and methods for determining the concentration of the constituents of a sample of harvested agricultural products. The analysis is performed during the harvesting process by means of a spectrometric arrangement in the near infrared range. The constituents of the sample are determined, expressed in a percentage, based on the reflection power of the sample with respect to certain wavelengths. The arrangement for determining the concentration is optically stable and consequently suited for use on agricultural equipment, such as combines. The measurement arrangement comprises a light source for irradiating the crop flow with a plurality of wavelengths, an optical receiver for receiving the reflected radiation, a wavelength separator for separating the received radiation, and a detector for generating intensity signals from the received, reflected and separated radiation. Only the measuring head, which comprises the light source and the receiver, is arranged in the direct vicinity of the measuring crop. The actual evaluation unit with the wavelength separator and detector is arranged, for example, in the cab of the harvester. Fiber optic lines are used to transmit the measured data from the measuring head to the evaluation unit. Since during the analysis of, for example, grain the absorption and reflection behavior fluctuates heavily from one sample to the next, constant calibration of the spectrometer is required. For this purpose a reference standard having a high reflection power, which can be motor-actuated and closes the optical path to the measuring crop for referencing, is arranged in the measuring head. Referencing generally occurs automatically by the control unit. The disadvantage with this solution is that vibrations associated with an operating harvesting machine cause modular interference in the optical fibers or can even damage them. One embodiment of the solution provides for a spatial separation between the measurement arrangement and the evaluation unit comprising a display unit. A connection of the evaluation unit to a harvester, however, is not provided.

WO 99/040419 describes a spectrometer for measuring the constituents of harvested agricultural products, which can be used particularly in combination with combines for real time analysis of grain. The spectrometer used here, which operates in the near infrared range (NIR), allows both chemical and physical properties of different materials to be analyzed. Contrary to ground grain, during the analysis of whole grain, for example, the absorption and reflection behavior fluctuates heavily from one sample to the next. It is necessary to constantly calibrate the spectrometer in order to still achieve accurately measured values. For this, the sample is typically replaced with a standard sample. The spectrometer then provides standard data for calibration of the measurement arrangement. The reflected light is conducted via fiber optic cables to a diffraction grating or an equivalent constituent and is depicted, split by the diffraction grating, on a detector or a detector array. By analyzing the intensity levels of the reflected radiation, the constituents can be determined, expressed in percent. The disadvantage with this solution is that the standard sample is arranged in the measuring head. While this takes various dynamic factors, such as changes in the light source, into consideration, influences arising from dirt on the window of the measuring head cannot be considered and affect the accuracy of the measurement results. Furthermore vibrations can lead to modular interference in the optical fibers or even damage them.

A harvesting machine comprising a sensor operating in the NIR range for measuring the contents and/or properties of crops is described in EP 1 053 671 B1. For the detection of organic constituents preferably wavelengths between 400 nm and 1.7 mm are employed. The sensor, which is arranged outside of an agricultural machine, is appropriately connected detachably to a suitable interface of a data acquisition device so that the properties of the crop picked up by the agricultural machine can be determined and/or crop mapping is possible. The captured measured data can be processed further especially using a computer. Additional sensors allow among other things the crop throughput and the current position (GPS) to be detected and be stored jointly with the measured values relating to the contents or the other parameters with georeferences.

In the still unpublished patent application DE 10 2004 021 448.4 a spectrometric reflection measuring head with internal recalibration is described, where the housing of the measuring head additionally comprises at least two standards, preferably a black and a white standard, for internal recalibration, which can be swiveled optionally in the optical path of the reflection measuring head. After the spectrometer has captured the measured data of both standards, the reflection measuring head is recalibrated by the control and evaluation unit. Additionally, prior to start-up of the measuring arrangement or at certain intervals, at least two external standards can be available for calibration of the reflection measuring head. The measuring head is connected to the spectrometer via fiber-optic lines.

A system for measuring constituents of agricultural products is described in U.S. Pat. No. 6,418,805. The system of this invention comprises a container for holding grain. A movable element is positioned within the container in order to move the grain within the container such that a grain flow is simulated. A probe analyzes the moving grain in real time, while different constituents of the moving grain are determined at the same time from the same grain portion. This detection system for grain samples is suited for the calibration of analysis systems already contained in a device used to process grain or installed thereon at a later time since the rotation of the grain within the container simulates the flow of the grain on a chute or in a line of such a device. A calibration of the device itself is not provided.

US 2002/0039186 A1 describes an arrangement and a method for the spectroscopic analysis of the physical and chemical properties of a sample. The measurement arrangement can be designed as a probe tip in order to be able to take a statistical sample, for example, of a truckload of grain and analyze it. The analysis here occurs while the entire sample is still located on the vehicle or in a container. Based on the properties of this sample, a conclusion is drawn about the properties and constituents of the entire sample. In another embodiment the grain can be analyzed during the unloading process by a measuring head, i.e. while it is in motion. Here nearly the entire sample can be analyzed in real time. For calibration purposes the measuring head comprises an aperture cover, which either allows the light reflected from the measurement object or the reference light to shine on the detector. The reference light is masked off from the optical path of the light source. The aperture cover can also be designed as a reference standard and be brought into a position in which no light shines on the detector in order to capture the dark signal. The existing electronic control system allows the system for the light source to be calibrated automatically. In the arrangement for the spectroscopic analysis, the actual measuring arrangement, which can be designed as a probe tip or measuring head, is connected to the actual control and evaluation unit via electric or fiber-optic lines.

Most systems used to determine the constituents of a sample, however, are designed for laboratory use. Moreover no robust sensors are available on the market that could emit the measured values directly to a bus system. Additionally black/white references are frequently required. The use of fiber optic cables in the measured section prevents the exploitation of a full aperture of the detector and represents a source for errors. The familiar sensors transmit their measured data via cables.

SUMMARY OF THE INVENTION

It is the object of the present invention to develop an arrangement for measuring the constituents of harvested agricultural products, which enables both static measurements as well as those on a material flow and is suited for use on harvesting machines and other equipment used in agriculture. The measurement arrangement shall be integrated in an existing bus system of the machine.

According to the invention the object is achieved with the features of the independent claims. Preferred embodiments and designs of the invention are the object of the dependent claims.

The spectrometric measuring head for harvesting machines and other equipment used in agriculture according to the invention consists of a housing comprising a window, in which a light source, a spectrometer arrangement and at least two standards for internal recalibration are arranged. These standards can optionally be swiveled in the optical path of the measuring head such that the entire measuring light coming from the light source is used for recalibration. An interface to a bus system and a processor are additionally arranged in the housing.

The suggested technical solution can be used for the specific measuring objective of determining the constituents of agricultural products during the harvesting process. Since the measuring head does not comprise any movable parts, it is extremely robust and suited for use on vehicles. The described measuring head allows both static measurements and measurements of a material flow. When evaluating the intensity distribution of the reflected radiation, different contents such as moisture, protein, starch or oil and properties such as cutting length, fiber state or temperature of the sample can be determined.

The measuring head is provided for applications in the NIR range in order to determine, for example, the moisture content and the content of fat, starch, protein and the like for samples from the agriculture and food industry.

For the use of different spectral regions the spectrometer arrangement must be adjusted accordingly; the measuring head can be used for the entire spectral region.

The invention will be explained in more detail hereinafter with reference to embodiments.

BRIEF DESCRIPTION OF THE DRAWINGS

FIG. 1 is the basic design of the spectrometric measuring head according to the invention.

DESCRIPTION OF THE PREFERRED EMBODIMENT

The spectrometric measuring head for harvesting machines and other equipment used in agriculture according to the invention comprises a housing 1 with a window 2, in which a light source 3, a spectrometer arrangement 4 and at least two standards 5 for internal recalibration are provided. These standards 5 can optionally be swiveled in the optical path of the measuring head such that the entire measuring light coming from the light source 3 is used for recalibration. Additionally a processor 11 for capturing and processing the measured values and an interface 12 to a bus system are arranged in the housing 1.

The window 2 in the housing 1, through which both the light source radiation and the radiation reflected by the sample 7 shines, is preferably made of sapphire. Sapphire enables a sufficiently long service life of the window 2, even with highly abrasive samples (e.g. samples 7 containing sand).

The lamp output of the light source 3, which preferably comprises a reflector 6, can be regulated automatically in order to adjust the spectrometer arrangement 4 to the various reflection behaviors of different samples 7. The lamp output is raised for samples 7 having a primarily dark color, without recalibrating the spectrometer arrangement. This ensures that the integration time of the spectrometer arrangement 4 remains nearly constant. In connection with the internal referencing thus measurements can be performed that are optimally adjusted to the respective sample and measuring conditions at all times. Controlling the lamp output can optimize the measured results especially for the automatic spectral processing performed by the processor 11.

The spectrometer arrangement 4 comprises at least one dispersion element 8 and one detector array 9 and may comprise depicting optical modules 10. Due to the direct depiction of the radiation reflected by the sample 7 on the detector array 9, depending on the sample 7 depictions of the structure of the sample 7 on the detector array 9 can lead to measurement errors. To prevent this, a light integrator is provided for homogenization purposes.

The two standards 5 included in the measuring head serve the internal recalibration of the measuring arrangement. At least two additional external standards (not illustrated) are provided in order to calibrate the measuring head before start-up of the measuring arrangement or at certain intervals. Preferably black and white standards are used both as internal 5 and as external standards, which may be supplemented with additional application-specific internal standards for farther-reaching recalibrations.

The standards are preferably motor-operated and can be controlled automatically and/or manually. Internal and external referencing enables automatic system monitoring, monitoring of the window 2 for damage, dirt etc. as well as the possibility of using different window materials without having to change or adapt the existing calibrations.

After detection of the measured data of the two internal standards 5 using the spectrometer arrangement 4, the measuring head is recalibrated using the measured values from the calibration of the reflection measuring head prior to start-up. After the internal standards 5 are swiveled out of the optical path, the measuring head is ready for the next measurement of the sample 7.

Although different measuring intensity levels of the light source 3 can be found on the internal measuring location than on the external sample measuring location, the geometric configuration of the internal standards 5 ensures that spectral intensity changes occur with equal proportionality in both measuring locations. Changes in sensitivity and the dark signal of the detector array 9 are equally effective, independent from the measuring location and therefore internally and externally. This way, the internal recalibration, which is conducted at predetermined intervals, can avoid a change in the measured value caused by the aforementioned influencing factors during long-term operation.

In the inventive solution the internal recalibration can occur at short intervals automatically following a previously established rhythm or as needed. Both the measuring head and the sample 7 remain in the normal measuring position during calibration and also recalibration.

The recalibration can be performed automatically after a certain time period (e.g. after 10 min.) has expired or also after discovering a non-plausible output value of the measuring head. Such a non-plausible output value exists, for example, when the output value of the measuring head is constant over a certain period of time (e.g. 10 seconds) or when it signals the presence of a crop although no crop flows through the feed channel, which can be verified based on the operating states of conveyor elements or based on other sensors, e.g. light barriers.

The interface 12 arranged in the measuring head to a bus system is preferably designed as a wireless connection for data transmission and/or calibration and/or system diagnosis and can support standards such as CAN, USB, RS232, Wireless LAN etc. However it is also conceivable to establish the connection from the measuring head to the bus system via electric and/or fiber-optic lines.

Additionally a processor 11 for capturing and processing the measured values is disposed in the housing. This processor 11 can generate both raw data, i.e. pre-processing of the data on a spectral basis, and calculated results, which can then be transmitted to a bus system via the interface 12. Moreover the processor 11 contains the software for the required bus management. The processor 11 creates a completely self-sufficiently operating system. To allow the measuring head to be used in a broad operating temperature range even without additional cooling of the detector array 9, the processor 11 comprises an appropriate compensating electronic system, which balances changing parameters of the detector array 9 in case of changes in the temperature.

In the inventive spectrometric measuring head for harvesting machines and other equipment used in agriculture the sample 7 that is supposed to be measured is exposed to radiation from a light source 3. The radiation reflected by the sample 7 is absorbed directly by the diode array 9 of the spectrometer arrangement 4. Based on the intensity distribution of the reflected radiation, different contents such as moisture, protein, starch or oil and properties such as cutting length, fiber state or temperature of the sample can be determined based on the calibrations. The described measuring head allows both static measurements and measurements of a material flow. Since the measuring head does not comprise any movable parts, it is extremely robust and suited for the use in vehicles.

Limiting the wavelength range allows the measuring head to be used in a broad temperature range without extensive and cost-intensive cooling.

With the arrangement according to the invention a spectrometric measuring head for harvesting machines and other equipment used in agriculture has been suggested, with which the constituents of harvested agricultural products can also be determined during the harvesting process on the harvester. The inventive measuring head can be used on stationary systems or any harvesting machine on which the crop flows past the measuring head, for example, in combines or forager, or in which the measuring head is moved past the crop, for example, on a swath.

The wireless communication of the measuring head to a control and evaluation unit facilitates the integration of the measuring head in an existing bus system of the harvester. The optional transmission of raw data for further processing or of the measured results for output gives the solution very flexible applications. The processor included in the measuring head and the automatic internal and external referencing create a completely self-sufficient operating system.

The internal recalibration offers the possibility of automatic system control, monitoring of the sample window for damage or dirt as well as the use of different window materials without having to change or adapt the existing calibrations.

Since the radiation reflected by the sample is depicted directly on the spectrometer, the system enables a high aperture. This results in greater sensitivity, a lower lamp output requirement, a lower sample temperature and smaller measuring errors.

Having described the preferred embodiment, it will become apparent that various modifications can be made without departing from the scope of the invention as defined in the accompanying claims.

The invention claimed is:

1. Spectrometric measuring head having an optical path for harvesting machines and other equipment used in agriculture comprising a housing, the housing having a window and supporting a light source providing a measuring light, a spectrometer arrangement and at least two standards, the standards providing internal recalibration, wherein the standards are supported for swiveling in the optical path of the measuring head such that the entire measuring light coming from the light source is used for the recalibration, and a processor for capturing and processing measured values and a bus system interface, wherein the processor and the bus system are arranged in the housing.

2. Spectrometric measuring head according to claim 1 wherein the light source includes a reflector and is automatically regulatable to adjust the spectrometer arrangement dependent on reflection behaviors of individual samples.

3. Spectrometric measuring head according to claim 1, in which the spectrometer arrangement comprises at least one dispersion element and a detector array.

4. Spectrometric measuring head according to claim 1, in which the spectrometer arrangement further comprises a depicting optical modules.

5. Spectrometric measuring head according to claim 1 including black and white standards for the internal recalibration.

6. Spectrometric measuring head according to claims 1, in which the standards are motor-operated and are operable in one or both of the following modes: automatic and manual.

7. Spectrometric measuring head according to claim 1, wherein one of the at least two standards is application-specific internal standards for recalibration.

8. Spectrometric measuring head according to claim 1, in which the interface (12) to a bus system is designed as a wireless connection for data transmission and/or calibration and/or system diagnosis.

9. Spectrometric measuring head according to claim 1 wherein the bus system interface comprises one of the following standards: CAN, USB, RS232, and Wireless LAN.

* * * * *